United States Patent
Goddard et al.

(10) Patent No.: US 6,565,895 B2
(45) Date of Patent: May 20, 2003

(54) BISMUTH COMPOUNDS FOR THE TREATMENT AND PREVENTION OF MUCOSITIS

(75) Inventors: Philip J. Goddard, West Newton, MA (US); Jeffrey D. Klinger, Sudbury, MA (US); Pradeep K. Dhal, Westford, MA (US); W. Harry Mandeville, III, Lynnfield, MA (US); Richard J. Fitzpatrick, Marblehead, MA (US); Thomas X. Neenan, Cambridge, MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/877,723

(22) Filed: Jun. 8, 2001

(65) Prior Publication Data

US 2002/0081340 A1 Jun. 27, 2002

Related U.S. Application Data

(60) Provisional application No. 60/210,313, filed on Jun. 8, 2000.

(51) Int. Cl.$^7$ .................. A61K 33/24; A61K 31/28; A61K 33/00; A61K 33/06
(52) U.S. Cl. .................. 424/653; 424/49; 424/53; 514/184; 514/503; 514/557; 514/574; 514/901; 514/902; 514/925; 514/928
(58) Field of Search ............... 424/653, 49, 53; 514/503, 901, 902, 925, 928, 184, 557, 574

(56) References Cited

U.S. PATENT DOCUMENTS

| | | | | |
|---|---|---|---|---|
| 2,259,492 A | | 10/1941 | Ruskin | 260/344 |
| 2,312,195 A | | 2/1943 | Ruskin | 260/344 |
| 2,427,692 A | | 9/1947 | Ruskin | 167/81 |
| 3,651,207 A | | 3/1972 | Lauster et al. | 424/50 |
| 3,651,208 A | * | 3/1972 | Lauster | 424/54 |
| 4,457,909 A | | 7/1984 | Tamés | 424/55 |
| 4,801,454 A | | 1/1989 | Coveney | 424/131 |
| 4,940,695 A | | 7/1990 | Coveny et al. | 514/57 |
| 5,013,560 A | | 5/1991 | Stentz et al. | 424/653 |
| 5,128,334 A | | 7/1992 | Nishikawa et al. | 514/159 |
| 5,234,908 A | * | 8/1993 | Szabo et al. | 514/12 |
| 5,281,196 A | | 1/1994 | Sultenfuss | 604/20 |

FOREIGN PATENT DOCUMENTS

| | | |
|---|---|---|
| SU | 1734760 A1 | 9/1989 |
| WO | WO 01/12128 A2 | 2/2001 |

OTHER PUBLICATIONS

Hild, Günter., "An Article Concerning Rectal Bismuth Therapy in Angina Tonsillaris, Pharyngitis and Inflammation of Mucous Membrane of the Mouth," *Medizinische*, 40:1879–1886 (1959). English translation of entire article included.

Sun et al., "Bismuth Antiulcer Complexes," *Topics in Biological Inorganic Chemistry*, 2:159–185 (1999).

Brian et al., "Bismuth Compounds and Preparations with Biological or Medicinal Relevance" *Chemical Reviews*, 99(9) :2601–2657 (1999).

Israel et al., "Topical Dehydroascorbic Acid (DHA) Reduces Moderate to Severe Mucositis in the Hamster Acute Radiation Model," *Program/Proceedings of the American Society of Clinical Oncology*. Thirty–sixth Annual Meeting, New Orleans, LA, May 20–23, 2000.

* cited by examiner

Primary Examiner—John Pak
(74) Attorney, Agent, or Firm—Hamilton, Brook, Smith &Reynolds, P.C.

(57) ABSTRACT

The invention relates to the unexpected discovery that bismuth-containing compounds are effective in the treatment of oral mucositis in a mammal. Thus, the invention relates, in one aspect to a method of treating oral mucositis comprising administering an effective amount of a pharmaceutically acceptable bismuth-containing compound, such as a bismuth salt or bismuth complex. In a preferred embodiment, the bismuth compound is an organic or inorganic salt such as, bismuth subsalicylate, bismuth subgallate, bismuth aluminate, bismuth citrate, bismuth subcitrate, bismuth carbonate, bismuth subcarbonate, tripotassium dicitrato bismuthate, bismuth nitrate, bismuth subnitrate, bismuth tartrate and mixtures thereof, preferably, bismuth subsalicylate and bismuth subgallate.

23 Claims, No Drawings

BISMUTH COMPOUNDS FOR THE TREATMENT AND PREVENTION OF MUCOSITIS

RELATED APPLICATIONS

This application claims the benefit of U.S. Provisional Application No. 60/210,313, filed Jun. 8, 2000, the entire teachings of which are incorporated herein by reference.

BACKGROUND OF THE INVENTION

Oral ulcerative mucositis is a common, painful, dose-limiting toxicity of drug and radiation therapy for cancer. The disorder is characterized by breakdown of the oral mucosa, which results in the formation of ulcerative lesions. In granulocytopenic patients, the ulcerations that accompany mucositis are frequent portals of entry for indigenous oral bacteria often leading to sepsis or bacteremia. Mucositis occurs to some degree in more than one third of all patients receiving anti-neoplastic drug therapy. The frequency and severity are significantly greater among patients who are treated with induction therapy for leukemia or with many of the conditioning regimens for bone marrow transplant. Among these individuals, moderate to severe mucositis (ulceration) is not unusual in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached.

Clinically mucositis progresses through four stages: (1) An initial stage that is characterized by inflammatory changes of erythema and edema. Localized islands of hyperkeratosis may also been seen. This stage is symptomatically mild and may be successfully palliated by topical anesthetics. (2) Subsequently the mucosa breaks down and becomes eroded and atrophic with increasingly significant inflammatory changes. This stage is increasingly painful and may require systemic analgesic therapy in the form of NSAIDs or oral narcotics for adequate palliation. (3) The third stage of mucositis is the most symptomatic. Full thickness ulcers of the mucosa cause severe discomfort necessitating parenteral narcotic therapy. In addition, in the myelosuppressive patient, these ulcerations provide a systemic portal of entry for the oral microflora often leading to bacteremia and sepsis. Antimicrobial intervention is required. (4) Finally, spontaneous healing occurs about 2–3 weeks after cessation of anti-neoplastic therapy.

The complexity of mucositis as a biological process has only been recently appreciated. The condition appears to represent a sequential interaction of oral mucosal cells and tissues including connective tissue, endothelium, epithelium and inflammatory cells, pro-inflammatory cytokines and local environmental factors such as bacteria and saliva. Damage to epithelial and connective tissue induces release of inflammatory cytokines leading to mucosal damage. Additionally, both direct and indirect effects to epithelial cells result in either apoptotic or necrotic changes in the basal layer; differentiation into new epithelial cells is halted. The arrest of epithelial cell renewal leads to atrophy followed by ulceration.

Standard therapy for mucositis is predominantly palliative, including application of topical analgesics such as lidocaine and/or systemic administration of narcotics and antibiotics. Thus, there is a need for new treatments which inhibit, prevent, reduce the severity, and/or promote the healing of mucositis.

SUMMARY OF THE INVENTION

The invention relates to the unexpected discovery that bismuth-containing compounds are effective in the treatment of oral mucositis in a mammal (see Example 7). Thus, the invention relates, in one aspect, to a method of treating oral mucositis comprising administering an effective amount of a pharmaceutically acceptable bismuth-containing compound, such as a bismuth salt or bismuth complex. In one preferred embodiment, the bismuth compound is an organic or inorganic salt such as, bismuth subsalicylate, bismuth subgallate, bismuth aluminate, bismuth citrate, bismuth subcitrate, bismuth carbonate, bismuth subcarbonate, tripotassium dicitrato bismuthate, bismuth nitrate, bismuth subnitrate, bismuth tartrate and mixtures thereof, preferably, bismuth subsalicylate and bismuth subgallate. Other examples include bismuth acetyl histidine, bismuth benzoate, bismuth salicylate basic, bismuth formate, bismuth acetate, bismuth propionate, bismuth butyrate and bismuth salicylate. In another preferred embodiment, the bismuth compound is the salt of an amino acid or a peptide, preferably an antimicrobial peptide (e.g., maganin, cecoropin and iseganin).

Another embodiment of the present invention is the described bismuth salts for use in the manufacture of a medicament for the treatment or prevention of oral mucositis.

DETAILED DESCRIPTION OF THE INVENTION

As stated above, the invention relates to the unexpected discovery that bismuth-containing compounds are effective in the treatment of oral mucositis in a mammal. Oral mucositis is defined herein as inflammation of a mucous membrane of the oral cavity or lips. Thus, the invention relates, in one aspect to a method of treating oral mucositis comprising administering an effective amount of a pharmaceutically acceptable bismuth-containing compound, such as a bismuth salt or bismuth complex. In one preferred embodiment, the bismuth compound is an organic or inorganic salt such as, bismuth subsalicylate, bismuth subgallate, bismuth aluminate, bismuth citrate, bismuth subcitrate, bismuth carbonate, bismuth subcarbonate, tripotassium dicitrato bismuthate, bismuth nitrate, bismuth subnitrate, bismuth tartrate and mixtures thereof, preferably, bismuth subsalicylate and bismuth subgallate. Other examples include bismuth acetyl histidine, bismuth benzoate, bismuth salicylate basic, bismuth formate, bismuth acetate, bismuth propionate, bismuth butyrate and bismuth salicylate. In another preferred embodiment, the bismuth compound is the salt of an amino acid or a peptide, preferably an antimicrobial (e.g., maganin, cecoropin and iseganin). Additionally, the invention includes the use of the described bismuth-containing compounds for use in the manufacture of a medicament for the treatment or prevention of oral mucositis.

Bismuth-containing compounds and pharmaceutical compositions thereof suitable for use in the present invention are generally known in the art. Various bismuth salts and complexes have been described for use in the treatment of various gastrointestinal disorders, including peptic ulcers of the esophagus, stomach or duodenum and for preventing gastrointestinal distress. These formulations include Pepto-Bismol® (the Proctor & Gamble Company, bismuth subsalicylate in a methylcellulose/magnesium aluminum silica suspension). See, also, U.S. Pat. Nos. 5,013,560, 4,801,454 and 4,940,695, the contents of which are incorporated herein by reference.

When the bismuth-containing compound is a salt, bismuth is preferably in the +3 oxidation state but can also be in the +5 oxidation state. The counteranions in the bismuth salt can all be the same, or, in the alternative, can be different. Bismuth salts which contain two or more different counteranions are said to be "mixed". Alternatively, the bismuth-containing compound can be bismuth metal, i.e., bismuth in the zero oxidation state.

In another preferred embodiment, the bismuth salt is the salt of a non-steroidal anti-inflammatory agent (hereinafter "NSAID"). Preferred NSAIDs have at least one acidic functional group, such as a carboxylic acid, sulfonic acid, phosphoric acid, sulfinic acid, phenol or thiol functional group, so that the compound can readily form an anion and bond ionically with bismuth. Specific examples of suitable NSAIDs include aminoarylcarboxylic acid derivatives (e.g., Enfenamic Acid, Etofenamate, Flufenamic Acid, Isonixin, Meclofenamic Acid, Niflumic Acid, Talniflumate, Terofenamate and Tolfenamic Acid), arylacetic acid derivatives (e.g., Acematicin, Alclofenac, Amfenac, Bufexamac, Caprofen, Cinmetacin, Clopirac, Diclofenac, Diclofenac Sodium, Etodolac, Felbinac, Fenclofenac, Fenclorac, Fenclozic Acid, Fenoprofen, Fentiazac, Flubiprofen, Glucametacin, Ibufenac, Ibuprofen, Indomethacin, Isofezolac, Isoxepac, Ketoprofen, Lonazolac, Metiazinic Acid, Naproxen, Oxametacine, Proglumrtacin, Sulindac, Tenidap, Tiramide, Tolectin, Tolmetin, Zomax and Zomepirac), arylbutyric acid ferivatives (e.g., Bumadizon, Butibufen, Fenbufen and Xenbucin) arylcarboxylic acids (e.g., Clidanac, Ketorolac and Tinoridine), arylproprionic acid derivatives (e.g., Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Piroprofen, Pranoprofen, Protinizinic Acid, Suprofen and Tiaprofenic Acid), pyrazoles (e.g., Difenamizole and Epirizole), pyrazolones (e.g., Apazone, Benzpiperylon, Feprazone, Mofebutazone, Morazone, Oxyphenbutazone, Phenylbutazone, Pipebuzone, Propyphenazone, Ramifenazone, Suxibuzone and Thiazolinobutazone), salicyclic acid derivatives (e.g., Acetaminosalol, 5-Aminosalicylic Acid, Aspirin, Benorylate, Biphenyl Aspirin, Bromosaligenin, Calcium Acetylsalicylate, Diflunisal, Etersalate, Fendosal, Flufenisal, Gentisic Acid, Glycol Salicylate, Imidazole Salicylate, Lysine Acetylsalicylate, Mesalamine, Morpholine Salicylate, 1-Naphthyl Sallicylate, Olsalazine, Parsalmide, Phenyl Acetylsalicylate, Phenyl Salicylate, 2-Phosphonoxybenzoic Acid, Salacetamide, Salicylamide O-Acetic Acid, Salicylic Acid, Salicyloyl Salicylic Acid, Salicylsulfuric Acid, Salsalate and Sulfasalazine), thiazinecarboxamides (e.g., Droxicam, Isoxicam, Piroxicam and Tenoxicam), ϵ-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Ketorolac, Meclofenamic Acid, Mefenamic Acid, Nabumetone, Nimesulide, Orgotein, Oxaceprol, Paranyline, Perisoxal, Pifoxime, Piroxicam, Proquazone and Tenidap.

In another preferred embodiment, the bismuth salt is the salt of an antimicrobial agent. Preferred antimicrobial agents are those which have at least one acidic functional group, so that the compound can readily form an anion and bond ionically with bismuth. Specific examples of suitable antimicrobial agents include pencillins (e.g., Benzyl penicillin, P-hydroxybenzyl penicillin, 2-pentenyl penicillin, N-heptyl penicillin, phenoxymethyl penicillin, Phenethicillin, Methicillin, Oxacillin, Cloxacillin, Dicloxacillin, Flucloxacillino, Nafcillin, Ampicillin, Amoxicillin, Cyclacillin, Carbenicillin, Ticarcillin, Piperacillin, Azlocillin, Meczlocillin, Mecillinam, Amdinocillin), Cephalosporin and derivatives thereof (e.g, Cephalothin, Cephapirin, Cephacetrile, Cephazolin, Caphalexin, Cephandine, Cefadroxil, Cefamandol, Cefuroxime, Ceforanide, Cefoxitin, Cefotetan, Cefaclor, Cefotaxime, Ceftizoxime, Ceftrioxone, Ceftazidime, Moxalactam, Cefoperazone, Cefixime, Ceftibuten and Cefprozil), Oxolinic Acid, Amifloxacin, Temafloxacin, Nalidixic Acid, Piromidic Acid, Ciprofloxacin, Cinoxacin, Norfloxacin, Perfloxacin, Rosaxacin, Ofloxacin, Enoxacin, Pipemidic Acid, Sulbactam, Clavulinic Acid, β-Bromopenicillanic Acid, β-Chloropenicillanic Acid, 6-Acetylmethylene-Penicillanic Acid, Cephoxazole, Sultampicillin, Formaldehyde Hudrate Ester of Adinocillin and Sulbactam, Tazobactam, Aztreonam, Sulfazethin, Isosulfazethin, Norcardicins, m-Carboxyphenyl Phenylacetamidomethylphosphonate, Chlortetracycline, Oxytetracyline, Tetracycline, Demeclocycline, Doxycycline, Methacycline and Minocycline.

In another preferred embodiment, the bismuth salt is mixed and is the salt of an antimicrobial agent and an NSAID.

In another preferred embodiment, the bismuth salt is one of the salts described above, provided however, that the salt does not comprise an antioxidant or free radical scavenger.

In another preferred embodiment, the bismuth salt is mixed and is the salt of an antimicrobial agent and an antioxidant or free radical scavenger. Suitable antioxidants and free radical scavengers generally have at least one acidic functional group, so that the antioxidant or free radical scavenger can readily form an anion and bond ionically with bismuth. In a preferred embodiment, the antioxidant or free radical additionally comprise a phenol, a phoshorothioate, a thiol or one or more double bonds which readily oxidize or readily react with free radicals. Examples of suitable phenol-containing compounds include 2,6-di-tert-butyl-4-methoxy phenol, 2,6-di-tert-butyl-4-methyl phenol, α-tocopherol, retinoic acid and catechol; examples of suitable thiol-containing compounds include N-acetylcysteine, mercaptoethylamine and glutathione; examples of suitable phosphorothioates include amifostine; and examples of suitable double bond-containing compounds include ascorbic acid and dehydroascorbic acid.

In yet another preferred embodiment, the bismuth salt is mixed and is the salt of an NSAID and an antioxidant or free radical scavenger.

The bismuth-containing compound is generally locally administered to the lesion in the mouth. This can be accomplished by administering an aqueous suspension of the compound or by administering a powder or tablet which is then masticated. The composition can be applied directly to the lesion, e.g., by a swab, or by other means, such as in a mouthwash or rinse. Preferably, the compound is administered as a suspension, either by a swab or by a rinse.

An "effective amount" of the compound or composition is the quantity which results in a desired therapeutic or prophylactic effect with respect to oral mucositis. "A desired therapeutic effect" includes an amelioration of the discomfort associated with the oral mucositis and/or an increase in the rate of healing of lesions associated with oral mucositis. A "desired prophylactic effect" includes a reduced number of lesions and/or reduced size of mucositis lesions compared with, for example, what is normally experienced by a mammal undergoing cancer therapy. Typically, an "effective amount" is between about 0.1 mg/day to about 10 grams/day applied to or contacted with the lesion(s) or oral mucosal surface, and preferably between about 1.0 mg/day to about 1 gram/day and more preferably between about 10 mg/day to about 500 mg/day.

The composition can be administered to the patient as needed to provide amelioration or prevention (inhibition) of the symptoms. For example, the composition can be administered one, two, three, four or more times daily. In another embodiment, the composition is administered following meals and/or other fluid intake and/or as the saliva dissolves or removes the composition from the lesions.

Preferred suspensions of the bismuth-containing compound include aqueous suspensions further comprising an anionic or a non-ionic cellulose ether. Examples of nonionic cellulose ethers include alkyl-celluloses (e.g., methylcellulose), hydroxyalkylalkylcelluloses (e.g., hydrocyclopropylmethylcellulose; hydroxybutylmethylcellulose; hydroxyethylmethylcellulose; ethylhydroxyethylcellulose), hydroxyalkylcelluloses (e.g., hydroxyethylcellulose; hydroxypropylcellulose), and mixtures thereof. Most preferred are alkylcelluloses, especially methylcellulose. Pharmaceutically-acceptable non-ionic cellulose ether polymers are well known in the art, and are described in more detail in "Handbook of Water-Soluble Gums and Resins" (McGraw-Hill Book Company, New York; 1980; Davidson, editor), chapters 3, 12, and 13, the disclosures of which are incorporated herein by reference in their entirety. An anionic cellulose ether includes carboxymethyl cellulose.

Representative examples of pharmaceutically-acceptable non-ionic cellulose ether polymers useful in the compositions of the present invention are: Methocel A® (methylcellulose, sold by the Dow Chemical Company); Metolose SM® (methylcellulose, sold by Shin Etsu Chemical Products Ltd.); and Methocel E® (hydroxypropylmethylcellulose, sold by the Dow Chemical Company).

The pharmaceutical compositions of the present invention typically comprise, by weight, from about 0.1% to about 25% or more of a non-ionic cellulose ether polymer, preferably from about 0.1% to about 10%, more preferably from about 0.5% to about 3%, and most preferably from about 0.5% to about 1.5%.

Alternatively or additionally, the composition can contain other high molecular weight polysaccharides, such as a xanthan or guar gum. Xanthan gum is available from a variety of commercial sources, including Rhodigel® (sold by Rhone Poulenc Industries) and Keltrol® (sold by Kelco Division of Merck & Co., Inc.). Xanthan gum is typically used at a level of from about 0.1% to about 5%, preferably from about 0.1% to about 3%, and more preferably from about 0.5% to about 1.5%.

The suspension further preferably comprises a magnesium aluminum silcate. Magnesiuim aluminum silicate (or aluminum magnesium silicate) is of the formula $Al_2MgO_8Si_2$, occurring naturally in such smectite minerals as colerainite, saponite, and sapphirine. Refined magnesium aluminum silicates useful herein are readily available, such as Veegum®, magnesium aluminum silicate, manufactured by R. T. Vanderbilt Company, Inc.

The pharmaceutical compositions of the present invention typically comprise, by weight, from about 0.1% to about 25% or more of a magnesium aluminum silicate, preferably from about 0.1% to about 10%, more preferably from about 0.1% to about 5%, and most preferably from about 0.1% to about 5%, and most preferably from about 0.5% to about 1.5%.

In addition to the essential components described hereinbefore, the pharmaceutical compositions of the present invention may comprise additional optional components selected as appropriate for the particular orally-administrable dosage form being used. Various oral dosage forms can be used, including such solid forms as tablets, capsules, granules and bulk powders, as well as the preferred aqueous liquid forms. Tablets can be compressed, tablet triturates, sugar-coated, film-coated or multiple compressed, containing suitable binders, lubricants, diluents, disintegrating agents, coloring agents, flavoring agents, flow-inducing agents, and melting agents.

Liquid oral dosage forms are preferred herein. Compositions herein in the form of a liquid include, for example, aqueous solutions, emulsions, suspensions, solutions and/or suspensions reconstituted from non-effervescent granules and effervescent preparations reconstituted from effervescent granules. They may contain suitable solvents, preservatives, emulsifying agents, suspending agents, diluents, sweeteners, melting agents, coloring agents, and/or flavoring agents. Preferably, these liquid dosage forms comprise water, typically at a level by weight of from about 75% to about 99%, preferably from about 85% to about 98%, and most preferably from about 92% to about 96%.

Some examples of substances which can serve as pharmaceutically-acceptable optional components are sugars such as lactose, glucose and sucrose; starches such as corn starch and potato starch; powdered tragacanth; malt; gelatin; talc; stearic acid; magnesium stearate; calcium sulfate; and polyols such as propylene glycol, glycerine, sorbitol, mannitol, polyethylene glycol, benzoic acid, methylsalicylate, salicylic acid, and salts thereof, sodium saccharin, sorbic acid, aspartame, acesulfome and cyclamate. Wetting agents and lubricants such as sodium lauryl sulfate, as well as coloring agents, flavoring agents, excipients, tableting agents, stabilizers, anti-oxidants (preferably antioxidants which do not have acidic functional groups) and preservatives can also be present.

The choice of pharmaceutically-acceptable optional components to be used in the compositions of the present invention is basically determined by the form and aesthetic properties desired for the composition. Pharmaceutically-acceptable optional components suitable for the preparation of compositions herein for oral administration are well known in the art. Their selection will depend on secondary considerations like taste, cost, and shelf stability, which are not critical for the purposes of the present invention, and can be made without difficulty by a person skilled in the art.

In one preferred embodiment, the suspension employed herein is Pepto-Bismol® (containing 1.75% bismuth subsalicylate, about 1% methylcellulose and about 1% Veegum®) or an equivalent suspension omitting the flavorant and/or colorant. Other bismuth-containing composition include De-Nol® (bismuth subcitrate; Gist-Brocades, N.V.), Noralac® (bismuth aluminate, alginic acid and magnesium carbonate; North American Pharmaceuticals), Roter® bismuth (bismuth subnitrate; Roter Laboratories), and Fensobar Polvo® (bismuth subcarbonate, USV Pharmaceutical Corp.).

In yet another embodiment, the composition further comprises an antimicrobial agent (e.g., antibacterial, antiviral and antifungal agents), such as chlorhexidine, triclosan, iodine complexes, tetracyclines, metronidazole, bacitracin, neomycin, polymyxin B, tobramycin, vidariabine, denavir, acyclovir, gancyclovir, foscarnet, famcyclovir, nystatin, emphotericin, flucytocine, itraconazole, fluconazole, clotrimazole, and econazole, to prevent or treat infections of the lesions. The antimicrobial agent can also be a polymer, such as the antimicrobial polymers disclosed in Mandeville, III et al., "Ionic Polymers as Anti-Infective Agents", U.S. Pat. No. 6,034,129, and Kurtz and Neenan; "Antimicrobial Compositions and Methods", U.S. Ser. No. 09/568,825, filed May 11, 2000 which is now U.S. Pat. No. 6,482,402; and Kurtz and Fitzpatrick, "Anionic Polymers as Toxin Binders", U.S. Ser. No. 09/541,268, filed Apr. 3, 2000 which is now U.S. Pat. No. 6,270,755.

Alternatively or additionally, the composition can further comprise an anti-inflammatory agent, such as aspirin, acetaminophen or ibuprofen, salicylic acid, salicyloyl salicylic acid (disalcid), salicylamide, diflunisal (dolobid), mefenamic acid (ponstel), mellofenamic acid (meclomen), fenoprofen (nalfon), ketoprofen (orodis), flubiprofen (ansaid), naproxen (naprosyn), diclofenas (voltaren), benorylate (benoral), caprofen (rimadyl), sulindac (clinoril), piroxicam, oxyphenylbutazone (tanderil), phenylbutazone (butazolidin), metiazinic acid, zomepirac, zomax, ketorolac (toradol), etodolac (Iodine), tolmetin, tolectin, indomethacin (indocin), tenidap (enablex) and/or an anesthetic agent, such as benzydamine, dyclonine, diphenylhydramine, benzocaine, cocaine and lidocaine.

The method of the claimed invention is particularly useful in the treatment of oral mucositis resulting from anti-cancer therapy, such as radiation therapy or chemotherapy, including induction therapy in leukemia patients. "Treatment" includes both prophylactic and/or therapeutic treatment. The treatment can be particularly beneficial for patients undergoing treatment for tumors of the head and neck, such as radiation patients. For prophylactic treatment of mucositis resulting from chemotherapy, treatment with the bismuth salt is initiated before the onset of the chemotherapy, during chemotherapy, after chemotherapy is completed but before symptoms appear or any combination of the above. For prophylactic treatment of mucositis resulting from radiation therapy, treatment with the bismuth salt is initiated before the onset of radiation therapy, during radiation exposure, after radiation exposure has been terminated (preferably no sooner than about one hour, more preferably five hours after termination) but before symptoms appear or any combination of the above. Prophylactic treatment includes inhibiting the onset of mucositis, delaying the onset of mucositis, reducing the severity of mucositis and/or reducing the likelihood of developing mucositis. For therapeutic treatment of mucositis resulting from radiation therapy or chemotherapy, the bismuth salt is administered after symptoms of mucusitis (e.g., mouth ulcers) have appeared.

The method is preferably used with human patients, but can also be used with other mammals, such as companion animals (e.g., dogs, cats, and the like), farm animals (horses, cattle and the like) and laboratory animals (hamsters, mice, rats and the like).

EXAMPLE 1

Synthesis of Bismuth Benzoate 5.79 grams of bismuth acetate (Aldrich) and three equivalents, 5.49 grams, of benzoic acid (Aldrich) were added to a 500 milliliter one neck round bottom flask. Toluene (300 milliliters) was then added as the solvent. A distillation head with 500 milliliters catch flask was attached to the reaction flask. The mixture was stirred vigorously and heated to reflux (about 110° C.). The mixture never completely dissolved (white cloudy mix). After about 5 hours of refluxing (while stirring), the toluene was slowly distilled off. When about 50 milliliters were left in the reaction flask, the heat was turned off and the reaction was allowed to cool to room temperature. A white powder precipitated and was separated by filtration. The resulting white powder was rinsed with about 1 liter of hexane, collected and dried overnight in vacuo at 50° C. The yield was 7.2 grams.

EXAMPLE 2

Synthesis of Bismuth Acetyl Histidine 2 grams of bismuth nitrate pentahydrate were added to 100 milliliters of deionized water in a 125 milliliter Erlenmeyer flask. The resulting mixture was stirred for about 4 hours (milky white mixture). The solution was then filtered by gravity filtration. A clear filtrate remained. 5.32 grams of N-acetyl histidine were added to a 250 milliliter one neck round bottom flask. Deionized water (15 milliliters) and NaOH (1.98 grams of 50% solution) were then added. The resulting mixture was stirred at room temperature until it became clear. Using an addition funnel, the bismuth nitrate solution in water was added dropwise to the reaction with stirring. This was stirred overnight at room temperature. A slightly cloudy solution remained. Nitrogen was blown over the reaction for about 24 hours to reduce the volume. The reaction was then placed in a refrigerator to precipitate more product. It was then centrifuged to reduce the solid particles to a pellet. The pellet was then washed with cold water (3×20 milliliters) and dried on the under vacuum at room temperature. The yield was 0.434 grams.

EXAMPLE 3

Synthesis of Bismuth Ascorbate Using Bismuth Acetate and Ascorbic Acid in Toluene 77.0 grams of bismuth acetate and one equivalent of ascorbic acid (35.12 grams) were added to a 2 liter round bottom flask. Toluene (1200 milliliters) was then added as the solvent. A distillation head with a 1 liter catch flask was attached to the reaction flask. The mixture was stirred vigorously and heated to reflux (about 110° C.). The mixture never completely dissolved (yellow cloudy mix). After about 5 hours of refluxing (while stirring), the toluene was slowly distilled off. When about 200 milliliters were left in the reaction flask, the heat was turned off, and the reaction was allowed to cool to room temperature. A fine yellow powder precipitated and was separated by filtration. The yellow powder with then rinsed with about 3 liters of hexane, collected and then dried in vacuo overnight at 50° C. The final product was a fine powder with a yellowish/off-white tint that had an acetic odor. The yield was 108 grams.

EXAMPLE 4

Procedure for Synthesizing Bismuth Glutathione Using Bismuth Acetate and Ascorbic Acid 9.4 grams of bismuth acetate (Aldrich) and three equivalents, 22.4 grams, of glutathione reduced (Lancaster) were added to a 1 liter one neck round bottom flask. Toluene (600 milliliters) was added as the solvent. A distillation head with a 500 milliliters catch flask was attached to the reaction flask. The mixture was stirred vigorously and heated to reflux (about 110° C.). The mixture never completely dissolved (white cloud mix). After about 5 hours of refluxing (while stirring), the toluene was slowly distilled off. When 100 milliliters were left in reaction flask, the heat was turned off and the reaction was allowed to cool to room temperature. A white powder precipitated and was separated by filtration. The resulting white powder was then rinsed with about 1 liter of hexane. The powder was then collected and placed on the speed vac overnight at 50° C. The resulting product was a white powder. This yield was 23.5 grams.

EXAMPLE 5

Synthesis of Bismuth Ascorbate Using $Na^+$ Ascorbate and Bismuth Nitrate 612.6 grams (10 equivalents) of sodium ascorbate (Aldrich) were dissolved in 1125 milliliters of deionized water (completely dissolved in about 15–20 minutes) in a 2 liter Erlenmeyer flask. The resulting solution was stirred at room temperature, resulting in a clear deep orange-red solution. 150 grams of bismuth nitrate pentahydrate (Aldrich) were ground into fine grains with a mortar and pestle. The ground bismuth nitrate was added as a solid a few hundred milligrams at a time over a period of approximately 3 hours. Upon addition of the bismuth nitrate, the solution became cloudy and small white undissolved particles could be seen. After all of the bismuth nitrate was added, the reaction was allowed to stir at room temperature for about 72 hours. It was then filtered by gravity filtration to remove any undissolved particles. A clear deep orange/red color remained. The filtrate was diluted with deionized water to 3750 milliliters and poured into a large 10 liter plastic bucket. The product was precipitated by adding 3750 milliliters ethanol (Aldrich, HPLC grade) to the reaction solution. It was then separated by filtration. The light orange solid that remained was dried under vacuum at room temperature. The yield was about 90 grams.

EXAMPLE 6

Procedure for Synthesizing Bismuth Ascorbate with Bismuth Acetate and Ascorbic Acid in Water Bismuth acetate (Strem Chemicals), 100 grams, was ground to a fine powder with a mortar and pestle. This fine powder was added to a 1 liter Erlenmeyer flask with 500 milliliters of deionized water with stirring, resulting in a suspension. With continuous stirring, 137 grams of ascorbic acid (Aldrich, 3 equivalents) were added as a solid. Immediately, a yellow color was observed. The total volume of the reaction was increased to 1 liter by adding deionized water. The reaction was stirred at room temperature for 5 days. After 5 days, the reaction was filtered using a Buchner funnel with suction. The isolated solid was air-dried in the Buchner funnel overnight. The final product was an orange-yellow solid. The reaction yielded 107 grams.

EXAMPLE 7

Bismuth-Containing Compounds Are Effective in Treating Mucositis in a Hamster Model Following Irradiation Therapy The efficacy of bismuth-containing compounds in treating oral mucositis was assayed according to a hamster model disclosed in Sonis et al., *Oral Oncology* 36:373 (2000), the entire teachings of which are incorporated herein by reference. Briefly, male Golden Syrian hamsters (Charles River Laboratories), aged 5 to 6 weeks, with body weights of approximately 90 g at project commencement, were used. Animals were individually numbered using an ear punch and housed in small groups of approximately 6 animals per cage. Animals were acclimatized for at least one week prior to project commencement. During this period, the animals were observed daily in order to reject animals that presented in poor condition. Animals were fed with a standard hamster chow and water ad libitum.

Mucositis was induced using an acute radiation protocol. A single dose of radiation (35–38 Gy/dose) was administered to all animals on Day 0. Radiation was generated with a 250 kilovolt potential (15 mA) source at a focal distance of 50 cm, hardened with a 0.35 mm Cu filtration system. Irradiation targeted the left buccal pouch mucosa at a rate of 121.5 cGy/minute. Prior to irradiation, animals were anesthetized with an intraperitoneal injection of sodium pentobarbital (80 mg/kg). The left buccal pouch was everted, fixed and isolated using a lead shield.

All animals were dosed with test material three times per day. A needleless tuberculin syringe containing 0.5 ml of the test compound was inserted into the left cheek pouch and the drug deposited into the pouch. Dosing began on Day 0 and continued until Day 19.

The mucositis score, weight change and survival were measured as outcomes in this study. For the evaluation of mucositis, the animals were anesthetized with inhalation anesthetics, and the left pouch everted. Mucositis was scored visually by comparison to a validated photographic scale, ranging from 0 for normal to 5 for severe ulceration (clinical scoring). In descriptive terms, this scale is defined as follows:

| Score | Description |
| --- | --- |
| 0 | Pouch completely healthy. No erythema or vasodilation |
| 1 | Light to severe erythema and vasodilation. No erosion of mucosa |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray appearance due to a pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation |
| 5 | Virtually all of pouch is ulcerated. Loss of pliability (pouch can only partially be extracted from mouth). |

A score of 1–2 is considered to represent a mild stage of the disease, whereas a score of 3–5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring). Treatment efficacy was measured by the amount of time in which the animals had a score of three or higher. A statistically significant decrease was considered to be an "improved score" and indicative that the treatment was effective in treating the mucositis.

Animals treated with solutions containing 1.75 mg/ml of bismuth ascorbate showed improvement in their mucositis scores; animals treated with solutions containing 3.5 mg/ml of bismuth subsalicylate, bismuth salicylate basic, bismuth citrate or bismuth benzoate showed improvement in their mucositis scores; and animals treated with solutions containing 17.5 mg/ml of bismuth glutathione showed improvement in their mucositis scores. Animals treated with bismuth (III) oxide, bismuth potassium tartrate, bismuth subcarbonate, bismuth subnitrate or bismuth subgallate did not show a statistically significant improvement when the treatment solution contained 17.5 mg/ml of test compound.

EXAMPLE 8

Bismuth Subsalicylate, Hamster Model with or Prior to Irradiation Therapy

Groups of 5 animals each (n=5). Dosing begins before irradiation and test compound can be applied with swabs according to the instructions below. No treatment is given after irradiation. Animals are scored for mucositis through day 20.

The hamsters are dosed with test compound 20 minutes prior to irradiation and then again 10 minutes prior to irradiation. Each dosing involves two applications of test compound. Twenty minutes before irradiation the applicator swab is dipped into the solution and allowed to soak for a few seconds and then is applied to the solution into the cheek pouch by liberally smearing the solution over the area to be irradiated as well as the surrounding areas that typically get mucositis. Thirty seconds—1 minute later the solution is reapplied. A fresh swab is used for each application. After 10 minutes the procedure is repeated. Ten minutes later the animals are irradiated. After irradiation the animals are not dosed again.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating oral mucositis in mammal comprising administering to a mammal in need of treatment for oral mucositis an effective amount of pharmaceutical agent selected from the group consisting of a pharmaceutically acceptable bismuth-containing compound and a pharmaceutically acceptable bismuth-containing compound in combination with one or more of an antimicrobial agent, an anti-inflammatory agent and an anesthetic agent, wherein said oral mucositis is a side-effect of anti-cancer therapy.

2. The method of claim 1 wherein the bismuth-containing compound is a bismuth salt or a bismuth complex.

3. The method of claim 1 wherein the pharmaceutically acceptable bismuth-containing compound is a bismuth salt.

4. The method of claim 3 wherein the bismuth salt is selected from the group consisting of bismuth subsalicylate, bismuth aluminate, bismuth citrate, bismuth subcitrate, bismuth carbonate, bismuth nitrate, bismuth tartrate and mixtures thereof.

5. The method of claim 4 wherein the bismuth salt is bismuth subsalicylate.

6. The method of claim 1 wherein the bismuth-containing compound is administered in an aqueous suspension.

7. The method of claim 6 wherein the suspension further comprises a non-ionic cellulose ether and magnesium aluminum silicate.

8. The method of claim 6 wherein the suspension further comprises a xanthan gum and magnesium aluminum silicate.

9. The method of claim 6 wherein the suspension further comprises one or more preservatives, colorants, sweeteners and flavorants.

10. The method of claim 6 wherein the suspension contains an antimicrobial agent.

11. The method of claim 6 wherein the suspension contains an anti inflammatory agent.

12. The method of claim 6 wherein the suspension contains an anesthetic agent.

13. The method of claim 3 wherein the bismuth salt is the salt of a non-steroidal anti-inflammatory agent.

14. The method of claim 3 wherein the bismuth salt is the salt of an antimicrobial agent.

15. The method of claim 3 wherein the bismuth salt is a mixed salt of a non-steroidal anti-inflammatory agent and an antimicrobial agent.

16. The method of claim 3 wherein the bismuth salt is a mixed salt of a non-steroidal anti-inflammatory agent and an antioxidant or a free radical scavenger.

17. The method of claim 3 wherein the bismuth salt is a mixed salt of an antimicrobial agent and an antioxidant or a free radical scavenger.

18. The method of claim 3 wherein the bismuth salt is bismuth acetyl histidine, bismuth benzoate, bismuth salicylate basic, bismuth formate, bismuth acetate, bismuth propionate, bismuth butyrate or bismuth salicylate.

19. The method of claim 3 wherein the bismuth salt is the salt of an amino acid or a peptide.

20. The method of claim 19 wherein the bismuth salt is the salt of an antimicrobial peptide.

21. The method of claim 1, wherein the anti-cancer therapy is radiation therapy.

22. The method of claim 1, wherein the anti-cancer therapy is chemotherapy.

23. The method of claim 1 wherein the mammal is administered an effective amount of the pharmaceutically acceptable bismuth compound alone.

* * * * *